United States Patent [19]

Suresh et al.

[11] Patent Number: 5,258,543
[45] Date of Patent: Nov. 2, 1993

[54] METHOD FOR AMMOXIDATION OF OLEFINS

[75] Inventors: Dev D. Suresh; Michael J. Seely; Maria S. Friedrich; Christos Paparizos, all of Cleveland, Ohio

[73] Assignee: The Standard Oil Company, Cleveland, Ohio

[21] Appl. No.: 904,611

[22] Filed: Jun. 26, 1992

[51] Int. Cl.$^5$ ............................................. C07C 253/26
[52] U.S. Cl. .................................. 558/325; 558/321; 558/323; 558/324
[58] Field of Search ................. 558/325, 321, 323, 324

[56] References Cited

U.S. PATENT DOCUMENTS

| | | | |
|---|---|---|---|
| 3,681,421 | 8/1972 | Barclay et al. | 260/465.3 |
| 3,860,534 | 1/1975 | Harris et al. | 558/325 X |
| 4,162,992 | 7/1979 | Wise | 260/465.3 X |
| 4,388,248 | 6/1983 | Wise | 558/325 |
| 5,008,427 | 4/1991 | Brazdil, Jr. et al. | 558/319 |

FOREIGN PATENT DOCUMENTS

| | | | |
|---|---|---|---|
| 41-3616 | 3/1966 | Japan | 558/325 |
| 1220527 | 1/1971 | United Kingdom | 558/325 |

*Primary Examiner*—Joseph Paul Brust
*Attorney, Agent, or Firm*—Charles S. Lynch; Michael F. Esposito; David J. Untener

[57] ABSTRACT

Disclosed is a method for ammoxidizing $C_3$ to $C_5$ mono-olefins to $\alpha,\beta$-mono-unsaturated acyclic nitriles having 3 to 5 carbon atoms and HCN by introducing such mono-olefins molecular oxygen and ammonia into a reaction zone into vapor phase contact with a solid ammoxidation catalyst, wherein the mol ratio of introduced molecular oxygen and ammonia to said introduced mono-olefin is at least 1.5 and 1.0, respectively, wherein said catalyst contains the elements and proportions indicated by the empirical formula:

$$V1Sb_aM_mN_nO_x$$

where
a = 0.5 to 2
M = one or more of: Sn, Ti, Fe, and Ga
m = 0.05 to 3, usually at least 0.1 and at most 1
N = one or more of: W, Bi, Mo, Li, Mg, P, Zn, Mn, Te, Ge, Nb, Zr, Cr, Al, Cu, Ce, B
n = 0.0 to 0.5, and wherein the preparation of the catalyst includes contacting in an aqueous dispersion a vanadium compound and an antimony compound while said vanadium is in solution.

11 Claims, No Drawings

METHOD FOR AMMOXIDATION OF OLEFINS

This invention relates to a method for the catalytic vapor phase ammoxidation of $C_3$ to $C_5$ olefins to $\alpha,\beta$-unsaturated mononitriles and HCN. In a more particular aspect the invention relates to a method for the catalytic vapor phase ammoxidation (1) of propylene to produce acrylonitrile and HCN and (2) isobutylene to produce methacrylonitrile and HCN. In the term "$\alpha,\beta$-unsaturated mononitriles", "unsaturated" means ethylenic unsaturation, and the term does not include acetylenic unsaturation.

The present method employs an oxidic catalyst containing V, Sb and one or more of Sn, Ti, Fe and Ga promoters which increase the activity.

U.S. Pat. No. 4,162,992 discloses the ammoxidation of olefins, especially propylene, using a catalyst having the formula $$Sb_aVTi_cO_x$$

where a is at least 6 and c is a number such that the ratio c/a is at least 0.5. As will be seen, however, the amount of Sb is far outside the range of the catalysts used in the presently claimed process.

In U.S. Pat. No. 3,681,421 to Barclay et al. there is disclosed the vapor phase catalytic ammoxidation of propylene over an oxide composition comprising antimony, vanadium and one or more additional polyvalent metals selected from tin, iron, cobalt and titanium in proportion 1 gm atom of antimony, 0.12 to 0.5 gm. atoms of vanadium and 0.25 to 0.5 gm atoms of each such additional polyvalent metal. This catalyst thus contains at least 2 atoms of Sb per atom of V, plus a minimum of ¼ atom each of the foregoing polyvalent metals which is present, thus overlapping the empirical formulas of the compositions of the catalysts used in the method of the present invention. The empirical formula of Example 1 of Barclay et al. is $VSb_2Sn$, and of Example 3 is $VSb_2Ti_{0.79}$ and thus overlap the empirical formula of the catalysts of the present invention. The catalysts used in the present method, however, are made in a different manner from the catalysts of the Barclay et al. patent that overlap the empirical formula of compositions of the catalyst of the present invention.

According to the present invention $C_3$ to $C_5$ mono-olefins are ammoxidized to $\alpha,\beta$-mono-unsaturated acyclic nitriles having 3 to 5 carbon atoms by introducing such mono-olefins, molecular oxygen and ammonia into a reaction zone into vapor phase contact with a solid ammoxidation catalyst, wherein the mol ratio of introduced molecular oxygen and ammonia to said introduced mono-olefin is at least 1.5 and 1.0, respectively, wherein said catalyst contains the elements and proportions indicated by the empirical formula:

$$V_1Sb_aM_mN_nO_x$$

where
a = 0.5 to 2
M = one or more of: Sn, Ti, Fe, and Ga
m = 0.05 to 3, usually at least 0.1 and at most 1
N = one or more of: W, Bi, Mo, Li, Mg, P, Zn, Mn, Te, Ge, Nb, Zr, Cr, Al, Cu, Ce, B
n = zero to 0.5,
and wherein the preparation of the catalyst includes contacting in an aqueous dispersion a vanadium compound and an antimony compound while said vanadium is in solution.

The term "unsaturated" in the preceding paragraph means carbon-to-carbon olefinic unsaturation. The product nitriles contain no acetylenic unsaturation.

In the present process the $C_3$ to $C_5$ olefin feed to the reaction zone can contain up to 10 mole percent $C_3$ to $C_5$ paraffins, based on the total moles of olefins plus paraffins. In this way relatively inexpensive olefin feedstock streams can be used without being highly purified. Usually, however, the hydrocarbon feed to the reaction zone is almost entirely $C_3$ to $C_5$ olefins except for small amounts of impurities.

The importance of the last clause in the foregoing statement of the invention is illustrated in the examples. Ammoxidation of propylene with Example 28 catalyst, a repeat of Example 1 catalyst of Barclay et al. gave a productivity of 0.09 pounds of acrylonitrile per pound of catalyst per hour. This is to be compared with a productivity of 0.34 of a catalyst of the same empirical composition (Example 9) when used in ammoxidation of propylene, wherein the catalyst was prepared in the manner of the present invention. Or the comparisons can be made using the same catalyst composition, wherein a portion of the Example 9 catalyst which was not washed was used (Example 10). There the productivity was 0.30 pounds of acrylonitrile per pound of catalyst per hour.

The productivity of the actual Example 1 of Barclay et al. was calculated to be only 0.032 pounds of acrylonitrile per pound of catalyst per hour.

The catalysts of U.S. Pat. No. 5,008,427 to Brazdil et al. and the present catalysts greatly overlap. They are used for the ammoxidation of paraffins in a process calling for a large excess of propane over both $O_2$ and $NH_3$. It is disclosed also that minor portions of olefins (such as propylene) can be present in the feed, although no actual working examples do have olefins in the feed. The highest acrylonitrile productivity in the large number of specific examples was 0.068 pounds of acrylonitrile per pound of catalyst per hour.

In the preparation of the catalysts used in the present process the calcination temperature must be over 750° C., more usually at least 780° C. Usual calcination temperatures are in the range 790° to 1050° C. While not being limited to any particular theory, we believe that the M elements increase the activity and stability of the $VSbO_4$ crystalline phase which is formed in making the catalyst of the formula. While the high temperature calcination of the catalyst precursor is needed to bring about increased acrylonitrile selectivity of the present catalyst composition, the calcination temperatures over 750° C. tend to cause decomposition of the active $VSbO_4$ phase and it is believed that the M elements not only increase the activity of the catalyst, but also perform the important function of stabilizing the active $VSbO_4$ crystalline phase.

While washing the finished, calcined catalyst with a lower alcohol, water, or an ammonium hydroxide solution usually somewhat increases the selectivity of conversion of the olefin, such as propylene to acrylonitrile, such treatments are not necessary.

The ammoxidation reaction is carried out at a temperature in the range from 350° C. to 700° C., but is usually in the range 430° to 520° C. The latter range is especially useful in the ammoxidation of propylene to acrylonitrile, plus HCN.

In the ammoxidation process of the present invention, the reaction is carried out in the gaseous phase by contacting a mixture containing the olefin, ammonia and molecular oxygen, and inert diluent, if any, conveniently in a fixed bed of the catalyst or a gravity flowing bed, a fluidized bed or a fast transport reactor mode.

Examples of applicable inert gaseous diluents are $N_2$, He, $CO_2$ and $H_2O$. In the present process in all its embodiments the volume ratio of inert gaseous diluent to olefin fed to the reaction zone is usually in the range zero to 8 (more often zero to 4).

The average contact time can often be from 0.01 to 10 seconds, but is usually from 0.02 to 5 seconds, more usually from 0.1 to 2 seconds.

The pressure in the reaction zone usually ranges from just over atmospheric up to 75, more usually up to 50, psia.

Nothing in the prior art remotely suggested the desirability of using catalysts having the empirical composition of Barclay et al. made by a process of Brazdil et al., U.S. Pat. No. 5,008,427. We have made the truly astounding discovery, however, that the catalyst compositions coming within the empirical formula recited in the claims and made by the method of the claims can catalyze the ammoxidation of olefins such as propylene at 2 to 5 or more times the rate of productivity of the best commercial catalysts, which has a productivity rate of about 0.10 pound of acrylonitrile per pound of catalyst per hour. This result is achieved at yields of acrylonitrile of over 65 percent and propylene conversion rates well over 90 percent.

Such remarkable results were extremely surprising and certainly unpredictable in the absence of actual data. The results of the experiments were a completely unexpected discovery not even contemplated by us in advance.

Another advantage of the use of the present catalysts over commercial catalysts is that generally much less acrolein is produced, thus simplifying the process for recovery of product acrylonitrile and HCN.

The catalysts used in the propylene ammoxidation reactions summarized in the tables were made as noted in the following examples. Some of the catalysts after calcining were washed with water or with an alcohol, and then dried. In these specific examples, Nalco is The Nalco Chemical Company of Chicago, Ill. Nyacol is Nyacol Products Inc., an affilate of the PQ Corporation of Ashland, Mass. DeGussa is Degussa Corporation, Teterboro, N.J., a subsidiary of Degussa AG, Frankfurt, Germany. Nissan is Nissan Chemical Industries, Ltd. of Tokyo, Japan.

The washing step with an alcohol or with water, referred to in some of the specific examples was effected by placing the catalyst in a coarse glass frit funnel, pouring alcohol or water over the catalyst, stirring in order to spread the catalyst evenly over the bottom of the funnel, then allowing the stated amount of the alcohol or water to pass over the catalyst without suction. It will be noted that very large amounts of water were needed compared to the amount of an alcohol needed in the examples. When water was used, distilled water was used and washing was continued until the conductivity of the effluent wash water reached that of the distilled water.

EXAMPLE 1

16.33 g $V_2O_5$ was added to mixture consisting of 540 cc $H_2O$ and 60.0 g of 30% $H_2O_2$ in a 2-liter beaker, and stirred at RT about 15 minutes, until a dark red peroxy complex had formed. 31.24 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 26.92 g of a 20% $SnO_2$ sol (Nalco 88SN123) was added, followed by 7.14 g of fumed $TiO_2$ (Degussa, P-25) and 100.0 g of a 40% $SiO_2$ sol (Nalco 2327). The catalyst slurry was evaporated on the hot plate with constant stirring until it thickened. It was then dired at 120° C. overnight and calcined at 290° C. for 3 hours, at 425° C. for 3 hours and at 650° C. for 8 hours. After this, the catalyst was ground and screened to a 20–35 mesh size. The ground catalyst was given a final calcination at 810° C. for 3 hours. Before being evaluated in the microreactor, 8.0 g of the calcined catalyst was Soxhlet extracted with MeOH for 1.5 hours and then dried at 120° C. The catalyst composition was 60% $VSb_{1.2}Sn_{0.2}Ti_{0.5}O_x$- 40% $SiO_2$.

EXAMPLE 2

A catalyst of the composition $VSb_{1.5}O_x$ was made as follows: 29.53 g $V_2O_5$ was added to a mixture consisting of 900 cc $H_2O$ and 100 g of 30% $H_2O_2$ in a 2-liter beaker, and stirred at RT about 15 minutes, until a dark red peroxy complex had formed. 70.63 g $Sb_2O_3$ powder was then added, the hot plate temperature control was set to "high", and the beaker was covered with a watchglass. As it heated, the color of the slurry changed from yellow to green to black. The mixture was digested for approximately 3 hours; water was added occasionally to keep the volume constant. The slurry was evaporated on the hot plate with constant stirring until it thickened. It was then dried at 120° C. overnight and calcined at 650° C. for 8 hours. After this, the catalyst was ground and screened to a 20–35 mesh size. The ground catalyst was given a final calcination at 810° C. for 3 hours. Before being evaluated in the microreactor, 10 g of the calcined catalyst was washed with 2 liters of water at RT and then dried at 120° C.

EXAMPLE 3

A catalyst of the composition $VSb_{1.4}Sn_{0.2}Ti_{0.2}O_x$ was made as follows: 26.8 g $V_2O_5$ was added to a mixture consisting of 900 cc $H_2O$ and 100 g of 30% $H_2O_2$ in a 2-liter beaker, and stirred at RT about 15 minutes, until a dark red peroxy complex had formed. 59.82 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 44.18 g of a 20% $SnO_2$ sol (Nalco 88SN123) was added, followed 4.68 g of $TiO_2$ powder. The slurry was evaporated on the hot plate with constant stirring until it thickened. It was then dried at 120° C. overnight.

The foregoing was repeated three times, and the four dried batches thoroughly blended into one large master batch. This was calcined at 650° C. for 8 hours. After this, the catalyst was ground and screened to a 20–35 mesh size. The ground catalyst was given a final calcination at 790° C. for 3 hours. Before being evaluated in a microreactor, 10.0 g of the calcined catalyst was washed with 6 liters of water at RT and then dried at 120° C.

(Note that the washing of a portion of the catalyst was omitted. When tested in the ammoxidation of propylene, it proved to be an active catalyst, but less active than the washed catalyst of this example.)

EXAMPLE 4

A catalyst having the empirical composition $VSb_2Sn_{0.5}O_x$ was made as follows: 7.93 g $V_2O_5$ was added to a mixture consisting of 360 cc $H_2O$ and 40 g of 30% $H_2O_2$ in a 2-liter beaker, and stirred at RT about 15 minutes, until a dark red peroxy complex had formed. 25.30 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 26.27 g of a 24.9% $SnO_2$ sol (Nyacol) was added. The slurry was evaporated on the hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 100 cc isobutanol at RT and then dried at 120° C.

EXAMPLE 5

A catalyst having the empirical formula $VSb_{1.4}Sn_{0.2}Ti_{0.1}Al_{0.001}O_x$ was made as follows: 27.43 g $V_2O_5$ was added to a mixture consisting of 900 cc $H_2O$ and 100 g of 30% $H_2O_2$ in a 2-liter beaker, and stirred at RT about 15 minutes, until a dark red peroxy complex had formed. 61.25 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 90.46 g of a 10% $SnO_2$ sol (Nalco 1160) was added, followed by 2.4 g of $TiO_2$ powder and 11.26 g of a 1.0 wt % $Al(NO_3)_3 \cdot 9H_2O$ solution. The slurry was evaporated on the hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 75 cc isobutanol at RT and then dried at 120° C.

EXAMPLE 6

A catalyst having the empirical formula 85% $VSb_{1.1}Sn_{0.2}$-15% $SiO_2$ was made as follows: 27.61 g $V_2O_5$ was added to a mixture consisting of 900 cc $H_2O$ and 100 g of 30% $H_2O_2$ in a 2-liter beaker, and stirred at RT about 15 minutes, until a dark red peroxy complex had formed. 48.43 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 85.08 g of a 10.7% $SnO_2$ sol (Nalco 1181D) was added, followed by 50 g of a 30% $SiO_2$ sol (Nalco). The slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was Soxhlet extracted with methanol for 1.5 hours and then dried at 120° C.

EXAMPLE 7

A catalyst of the empirical formula $VSb_{7.5}Cr_{2.5}O_x$ was made as follows: 3.33 g $V_2O_5$ was added to a mixture consisting of 60 cc $H_2O$ and 30 g of 30% $H_2O_2$ in a 2-liter beaker, and stirred at RT about 15 minutes, until a dark red peroxy complex had formed. Then 450 cc of $H_2O$ was added, followed by 39.78 g $Sb_2O_3$ powder, after which heating was continued for 30 minutes. Then 9.1 g $CrO_3$ was added and heating continued for another 2 hours. This slurry was evaporated on the hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours.

EXAMPLE 8

A catalyst having the empirical composition $VSb_{12}Ti_{15}O_x$ was made as follows: 1.5 g $V_2O_5$ was added to a mixture consisting of 30 cc $H_2O$ and 15 g of 30% $H_2O_2$ in a 2-liter beaker, and stirred at RT about 15 minutes, until a dark red peroxy complex had formed. Then 450 cc of $H_2O$ and 28.78 g of $Sb_2O_3$ powder were added and the slurry heated for 30 minutes. Then 19.72 g of $TiO_2$ powder slurried in a small amount of water was added and heating continued for 2 more hours. The slurry was evaporated on the hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours.

EXAMPLE 9

A catalyst of the empirical composition $VSb_2SnO_x$ was made as follows: 17.14 g $V_2O_5$ was added to a mixture consisting of 900 cc $H_2O$ and 100 g of 30% $H_2O_2$ in a 2-liter beaker, and stirred at RT about 15 minutes, until a dark red peroxy complex had formed. 54.68 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 264.17 g of a 10.7% $SnO_2$ sol (Nalco 1181D) was added. The slurry was evaporated on the hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst washed with 100 cc isobutanol at RT and then dried at 120° C.

EXAMPLE 10

This catalyst is a portion of the catalyst of the last example that was not washed.

EXAMPLE 11

A catalyst having the empirical composition $VSb_{1.2}Sn_{0.2}Ti_{0.5}O_x$ was made as follows: 27.21 g $V_2O_5$ was added to a mixture consisting of 900 cc $H_2O$ and 100 g of 30% $H_2O_2$ in a 2-liter beaker, and stirred at RT about 15 minutes, until a dark red peroxy complex had formed. 52.07 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 83.85 g of a 10.7% $SnO_2$ sol (Nalco 1181D) was added, followed by 11.89 g of fumed $TiO_2$ (Degussa, P-25). The slurry was evaporated on the hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 75 cc isobutanol at RT and then dried at 120° C.

EXAMPLE 12

This catalyst is a portion of the catalyst of the previous example that was not washed.

EXAMPLE 13

A catalyst having the empirical formula $VSb_{1.2}Sn_{0.2}TiO_x$ was made as follows: 24.32 g $V_2O_5$ was added to a mixture consisting of 900 cc $H_2O$ and 100 g of 30% $H_2O_2$ in a 2-liter beaker, and stirred at RT about 15 minutes, until a dark red peroxy complex had formed. 46.53 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 74.94 g of a 10.7% $SnO_2$ sol (Nalco 1181D) was added, followed by 21.26 g of fumed $TiO_2$ (Degussa, P-25). The catalyst slurry was evaporated on the hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours. Before being evaluated in the microreactor, 8.0 g of the calcined catalyst was washed with 150 cc isobutanol at RT and then dried at 120° C.

EXAMPLE 14

A catalyst having the empirical formula 85% $VSb_{1.2}Sn_{0.2}Ti_{0.5}O_x$-15% $SiO_2$ was made as follows: 23.13 g $V_2O_5$ was added to mixture consisting of 900 cc $H_2O$ and 100 g of 30% $H_2O_2$ in a 2-liter beaker, and stirred at RT about 15 minutes until a dark red peroxy complex had formed. 44.26 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 71.27 g of a 10.7% $SnO_2$ sol (Nalco 1181D) was added followed by 10.11 g of fumed $TiO_2$ (Degussa, P-25) and 50.0 g of a 30% $SiO_2$ sol (Nalco). The catalyst slurry was evaporated on the hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed by Soxhlet extraction with methanol and then dried at 120° C.

EXAMPLE 15

A catalyst having the empirical formula 60% $VSb_{1.2}Sn_{0.2}Ti_{0.5}O_x$-40% $SiO_2$ was made as follows: 16.33 g $V_2O_5$ was added to a mixture consisting of 540 cc $H_2O$ and 60 g of 30% $H_2O_2$ in a 2-liter beaker, and stirred at RT about 15 minutes, until a dark red peroxy complex had formed. 31.24 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 50.31 g of a 10.7% $SnO_2$ sol (Nalco 1181D) was added, followed by 7.14 g of fumed $TiO_2$ (Degussa, P-25) and 133.3 g of a 30% $SiO_2$ sol (Nalco). The catalyst slurry was evaporated on the hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours. Before being evaluated in the microreactor, 8.0 g of the calcined catalyst was washed with 150 cc isobutanol at RT and then dried at 120° C.

EXAMPLE 16

A catalyst having the empirical formula $VSb_{1.2}Sn_{0.2}Ti_{0.5}O_x$ was made as follows: 17.41 g $NH_4VO_3$ were dissolved in 1 liter of hot water. 26.03 g $Sb_2O_3$ powder was added and the slurry was refluxed for about 3 hours. 41.92 g of a 10.7% $SnO_2$ sol (Nalco-1181D) and 5.95 g of fumed $TiO_2$ (Degussa, P-25) were then added. The slurry was evaporated on a hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours. Before being evaluated in the microreactor, 8.0 g of the calcined catalyst was washed with 100 cc isobutanol at RT and then dried at 120° C.

EXAMPLE 17

A portion of the calcined catalyst of the last example was Soxhlet extracted with methanol for 1.5 hours instead of being washed with isobutanol.

EXAMPLE 18

A catalyst having the empirical formula 60% $VSb_{1.2}Sn_{0.2}Ti_{0.75}O_x$-40% $SiO_2$ was made as follows: 15.41 g $V_2O_5$ was added to a mixture consisting of 540 cc $H_2O$ and 60 g of 30% $H_2O_2$ in a 2-liter beaker, and stirred at RT about 15 minutes, until a dark red peroxy complex had formed. 29.49 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 25.40 g of a 20% $SnO_2$ sol (Nalco 88SN123) was added, followed by 10.1 g of fumed $TiO_2$ (Degussa, P-25) and 133.33 g of a 30% $SiO_2$ sol (Nalco). The slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 125 cc isobutanol at RT and then dried at 120° C.

EXAMPLE 19

A catalyst having the empirical formula $VSb_{1.2}Sn_{0.2}Ti_{0.5}O_x$ was made as follows: a solution of 17.41 g $NH_4VO_3$ dissolved in 600 cc hot water was added dropwise over a period of 2 hours to 26.03 g $Sb_2O_3$ powder slurried in 400 cc water. The mixture was digested for 1 hour. Then 37.38 g of a 12% $SnO_2$ sol (Nalco 1188) and 5.95 g of fumed $TiO_2$ (Degussa, P-25) were added. The slurry was evaporated on a hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours. Before being evaluated in the microreactor, 8.0 g of the calcined catalyst was washed by Soxhlet extraction with methanol for 1.5 hours and then dried at 120° C.

EXAMPLE 20

A catalyst having the empirical formula 60% $VSb_{1.2}Sn_{0.2}Ti_{0.5}K_{0.001}O_x$-40% $SiO_2$ was made as follows: 16.3 g $V_2O_5$ was added to a mixture consisting of 540 cc $H_2O$ and 60.0 g of 30% $H_2O_2$ in a 2-liter beaker, and stirred at RT about 15 minutes, until a dark red peroxy complex had formed. 31.24 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. A drop of the slurry was then tested on a filter paper to see whether it would bleed; since it did not, 26.9 g of a 20% $SnO_2$ sol (Nalco 88SN123) was added, followed by 7.13 g of fumed $TiO_2$ (Degussa, P-25) 0.18 g 10% $KNO_3$ solution in water and 100.0 g of a 40% $SiO_2$ sol (Nalco 2327). The slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8.0 g of the calcined catalyst was washed with 100 cc isobutanol at RT and then dried at 120° C.

EXAMPLE 21

A catalyst having the empirical formula 60% $VSb_{1.2}Sn_{0.2}Ti_{0.5}$-40% $SiO_2$ was made as follows: 27.21 g $V_2O_5$ was added to a mixture consisting of 900 cc $H_2O$ and 100 g of 30% $H_2O_2$ in a 2-liter beaker, and stirred at RT about 15 minutes, until a dark red proxy complex had formed. 52.07 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added to keep the volume constant. 83.85 g of a 10.7% $SnO_2$ sol (Nalco 1181D) was added, followed by 11.89 g of fumed $TiO_2$ (Degussa, P-25). The slurry was digested for 0.5 hr. and then there was added 222 g of a 30% $SiO_2$ sol (Nissan). The slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 100 cc isobutanol at RT and then dried at 120° C.

EXAMPLE 22

A catalyst having the empirical formula 60% $VSb_{1.2}SnO_{0.2}Ti_{0.5}O_x$-40% $SiO_2$ was made as follows: 16.33 g $V_2O_5$ was added to a mixture consisting of 540 cc $H_2O$ and 60.0 g of 30% $H_2O_2$ in a 2-liter beaker, and stirred at RT about 15 minutes, until a dark red peroxy complex had formed. 31.24 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 26.92 g of a 20% $SnO_2$ sol (Nalco 88SN123) was added, followed by 7.14 g of powdered $TiO_2$ and 133.33 g of a 30% $SiO_2$ sol (Nissan). The catalyst slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8.0 g of the calcined catalyst was washed with 100 cc isobutanol at RT and then dried at 120° C.

EXAMPLE 23

A catalyst having the empirical formula 60% $VSb_{1.2}Sn_{0.2}Ti_{0.5}$-40% $SiO_2$ was made as follows: 16.33 g $V_2O_5$ was added to a mixture consisting of 540 cc $H_2O$ and 60.0 g of 30% $H_2O_2$ in a 2-liter beaker, and stirred at RT about 15 minutes, until a dark red peroxy complex had formed. 31.24 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 26.92 g of a 20% $SnO_2$ sol (Nalco 88SN123) was added, followed by 7.14 g of fumed $TiO_2$ (Degussa, P-25) and 117.65 g of a 34% $SiO_2$ sol (Nalco H-1034). The catalyst slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8.0 g of the calcined catalyst

EXAMPLE 24

A catalyst having the empirical formula 60% $VSbSn_{0.2}Ti_{0.5}O_x$-40% $SiO_2$ was made as follows: 17.88 g $V_2O_5$ was added to a mixture consisting of 540 cc $H_2O$ and 60 g of 30% $H_2O_2$ in a 2-liter beaker, and stirred at RT about 15 minutes, until a dark red peroxy complex had formed. 28.51 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 29.47 g of a 20% $SnO_2$ sol (Nalco 88SN123) was added, followed by 7.81 g of fumed $TiO_2$ (Degussa, P-25) and 133.33 g of a 30% $SiO_2$ sol (Nissan). The catalyst slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 100 cc isobutanol at RT and then dried at 120° C.

EXAMPLE 25

This catalyst was prepared similarly to the first example except on a large scale. It had the same composition as that example. However, the procedure differed after formation of the slurry, which was concentrated somewhat by evaporation and then was spray dried in a pilot plant size spray dryer to make fluidizable microspheroidal catalyst. 4.5 pounds of the catalyst was recovered from the chamber and 3.5 pounds from the cyclone.

A 500 gram sample of the chamber product was calcined at 290° C. for 3 hours, 425° C. for 3 hours, 650° C. for 8 hours and 810° C. for 3 hours. 100 grams of this catalyst was washed with 1500 cc of isobutanol, and thereafter dried.

EXAMPLE 26

A catalyst having the empirical formula 60% $VSb_{1.2}Sn_{0.2}Ti_{0.5}O_x$ was made as follows: 16.33 g $V_2O_5$ was added to a mixture consisting of 900 cc $H_2O$ and 100 g of 30% $H_2O_2$ in a 2-liter beaker, and stirred at RT about 15 minutes, until a dark red peroxy complex had formed. 31.24 g $Sb_2O_3$ powder was then added, the hot plate temperature control was set to "high" and the beaker was covered a watchglass. As it heated, the color of the slurry changed from yellow to green to black. The mixture was digested for approximately 3 hrs; water was added occasionally to keep the volume constant. 50.3 g of a 20% $SnO_2$ sol (Nalco 88SN123) was added, followed by 7.14 g of fumed $TiO_2$ (Degussa, P-25) and 133.3 g of a 30% $SiO_2$ sol (Nalco). The catalyst slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened in a 20-35 mesh size. a The ground catalyst was given a final calcination at 810° C. for 3 hours. Before being evaluated in the microreactor, 8.0 g of the calcined catalyst was washed with 100 cc isobutanol at RT and then dried at 120° C.

EXAMPLE 27

A catalyst having the empirical formula 80% $VSB_{1.2}Ga_{0.2}Ti_{0.5}O_x$-20% $SiO_2$ was made as follows: 5.63 $V_2O_5$ was added to a mixture consisting of 450 cc $H_2O$ and 50.0 g of 30% $H_2O_2$ in a beaker, and stirred at RT about 15 minutes, until a dark red peroxy complex had formed. 10.78 g $Sb_2O_3$ powder was then added, the hot plate temperature control was set to "high", and the beaker was covered with a watchglass. As it heated, the color of the slurry changed form yellow to green to black. The mixture was digested for approximately 3 hrs; water was added occasionally to keep the volume constant. After dissolving in a small amount of water, 5.15 g of $Ga(NO_3)_3 \cdot 9H_2O$ was added, followed by 2.46 g of fumed $TiO_2$ (Degussa, P-25) and 16.67 g of a 30% $SiO_2$ sol (Nissan). The catalyst slurry was evaporated on the hot plate with constant stirring until it thickened. It was then dried at 120° C. over the weekend and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8.0 g of the calcined catalyst was washed with 75 cc isobutanol at room temperature and then dried at 120° C.

EXAMPLE 28

A catalyst having the empirical formula $VSb_2SnO_x$ was prepared as follows: 46.64 g of $Sb_2O_3$ powder was added during a period of 10 minutes to a stirred mixture of 240 g $H_2O$ and 80 g concentrated (70%) $HNO_3$, at 95°-100° C. 18.99 g of Sn metal powder (325 mesh size) was then added to the stirred suspension over a period of 30 minutes, while the temperature was maintained at 95°-100° C. Stirring at this temperature was continued for another 15 minutes; the slurry was then cooled and centrifuged. The solid cake was resuspended in 240 g $H_2O$ at 40° C. The pH of the slurry was raised to 7.0 by the addition of ~80 cc of a $NH_4OH$ solution consisting of 1/3 of 28% $NH_4OH$ and 2/3 $H_2O$. The slurry was stirred for another 5 minutes, the pH was readjusted to 7.0 and the slurry was centrifuged again. The solid cake was re-suspended in 240 cc $H_2O$ and recentrifuged. 14.63 g of $V_2O_5$ powder was added to the solid cake and mixed thoroughly. The wet paste was dried in a thin layer at 120° C. overnight. The dry powder was calcined at 290° C.-2 hrs., 425° C.-2 hrs., 650° C.-3 hrs. and at 850° C.-16 hrs.

EXAMPLE 29

This is a portion of the catalyst of the preceding example that was washed with isobutanol, using 75 cc to wash 8 g of catalyst. It was again dried at 120° C. overnight.

EXAMPLE 30

A catalyst having the empirical formula 60% $VSb_{1.2}Sn_{0.2}Ti_{0.5}O_x$-40% $SiO_2$ was made as follows: 8.16 g $V_2O_5$ was added to a mixture consisting of 450 cc $H_2O$ and 50 g of 30% $H_2O_2$ in a 2-liter beaker, and stirred at RT about 15 minutes, until a dark red peroxy complex had formed. 15.62 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 13.46 g of a 20% $SnO_2$ sol (Nalco 88SN123) was added, followed by 3.57 g of fumed $TiO_2$ (Degussa, P-25) and 33.33 g of a 30% $SiO_2$ sol (Nissan) and 10.0 g of fumed (Aerosil) $SiO_2$. The catalyst slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 100 cc isobutanol at RT and then dried at 120° C.

EXAMPLE 31

A catalyst having the empirical formula $VSB_{1.2}SnTiO_x$ was made as follows: 9.21 g $V_2O_5$ was added to a mixture consisting of 450 cc $H_2O$ and 50 g of 30% $H_2O_2$ in a 2-liter beaker, and stirred at RT about 15 minutes, until a dark red peroxy complex had formed. 17.62 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 75.89 g of a 20% $SnO_2$ sol (Nalco 88SN123) was added, followed by 8.05 g of fumed $TiO_2$ (Degussa, P-25). The catalyst slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 100 cc isobutanol at RT and then dried at 120° C.

EXAMPLE 32

A catalyst having the empirical composition $VSb_{1.2}Sn_{0.2}Ti_{0.5}O_x$ was made as follows: 27.21 g $V_2O_5$ was added to a mixture consisting of 900 cc $H_2O$ and 100 g of 30% $H_2O_2$ in a 2-liter beaker, and stirred at RT about 15 minutes, until a dark red peroxy complex had formed. 52.07 g $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 83.85 g of a 10.7% $SnO_2$ sol (Nalco 1181D) was added, followed by 11.89 g of fumed $TiO_2$ (Degussa, P-25). The slurry was evaporated on the hot plate with constant stirring until it thickened. It was then dried at 120° C. overnight and calcined at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 75 cc isobutanol at RT and then dried at 120° C.

EXAMPLE 33

A catalyst having the empirical formula $VSb_{1.2}Sn_{0.5}Ti_{0.5}$ was made as follows: 11.99 g $V_2O_5$ was added to a mixture consisting of 450 cc $H_2O$ 50 g of 30% $H_2O_2$ in a 2-liter beaker, and stirred at RT about 15 minutes, until a dark red peroxy complex had formed. 22.95 g $Sb_2O_3$ powder was then added, the hot plate temperature control was set to "high", and the beaker was covered with a watchglass. As it heated, the color of the slurry changed form yellow to green to black. The mixture was digested for approximately 3 hrs; water was added occasionally to keep the volume constant. 49.42 g of a 20% $SnO_2$ sol (Nalco 88SN123) was added, followed by 5.24 g of fumed $TiO_2$ (Degussa, P-25). The catalyst slurry was evaporated on the hot plate with constant stirring until, it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 100 cc isobutanol at RT and then dried at 120° C.

EXAMPLE 34

A catalyst having an empirical composition 70% $VSbSn_{0.2}O_x$ was made as follows: 13.46 g of $V_2O_5$ was added to a mixture consisting of 450 ml water and 50 g of 30% $H_2O_2$ in a 1 liter beaker, and stirred at RT about 15 minutes, until a dark red peroxy complex had formed. 32.18 g of $Sb_2O_3$ powder were then added, the not plate temperature control was set to "high", and the beaker was covered with a watch glass. As it heated, the color of the slurry changed from yellow to green to black. The mixture was digested for approximately 3 hours; water was added occasionally to keep the volume constant. 17.82 g of 25% $SnO_2$ sol (Nyacol) were added and the slurry heated an additional 1 hour. The slurry was then cooled and centrifuged free of unreacted $Sb_2O_3$ to give a black aqueous sol with 10.02% solids content. 123.1 g of the above were combined with 9.23 g of 40% $SiO_2$ sol (Nalco 41D01) and evaporated on a hot plate and then dried over night at 120° C. to give 15.58 g. This solid was further heated at 425° C. for 3 hours and 650° C. for 8 hours. The solid was then ground to give 7.61 g-20+35 mesh particles. This solid was finally heated at 810° C. for 3 hours and then washed with 22 liters of water.

EXAMPLE 35

A catalyst having an empirical composition 60% $VSb_{1.4}Sn_{0.2}Ti_{0.5}$-40% was made as follows: 15.02 g of $V_2O_5$ was added to a mixture consisting of 540 cc $H_2O$ and $SiO_2$ and 60 g of 30% $H_2O_2$ in a 2-liter beaker, and stirred at RT about 15 minutes, until a dark red peroxy complex had formed. 33.54 g $Sb_2O_3$ powder was then added, the hot plate temperature control was set to "high", and the beaker was covered with a watchglass. At it heated, the color of the slurry changed from yellow to green to black. The mixture was digested for approximately 3 hrs; water was added occasionally to keep the volume constant. 24.77 g of a 20% $SnO_2$ sol (Nalco 88SN123) was added, followed by 6.57 g of fumed $TiO_2$ (Degussa, P-25) and 133.33 g of a 30% $SiO_2$ sol (Nissan). The catalyst slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20-35 mesh size. The ground catalyst was given a final calcination at 810° C. for 3 hours. Before being evaluated in the microreactor, 8 g of the calcined catalyst was washed with 100 cc isobutanol at RT and then dried at 120° C.

EXAMPLE 36

A catalyst having the empirical formula 85% $VSb_{1.2}Sn_{0.5}Ti_{0.5}O_x$ was made as follows: 10.19 $V_2O_5$ was added to a mixture consisting of 450 cc $H_2O$ and 50.0 of 30% $H_2O_2$ in a beaker and stirred at RT about 15 minutes, until a dark red peroxy complex had formed. 19.50 $Sb_2O_3$ powder was then added, the hot plate temperature control was set to "high", and the beaker was covered with a watchglass. As it heated, the color of the slurry changed from yellow to green to black. The mixture was digested for approximately 3 hrs; water was added occasionally to keep the volume constant. 42.01 of a 20% $SnO_2$ sol (Nalco 88SN123) was added, followed by 4.45 g of fumed $TiO_2$ (Degussa, P-25) and 25.0 g of a 30% $SiO_2$ sol (Nissan). The catalyst slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20–35 mesh size. The ground catalyst was given a final calcination at 810° C. for 3 hours. Before being evaluated in the microreactor, 8.0 g of the calcined catalyst was washed with 125 cc of isobutanol and then dried at 120° C.

EXAMPLE 37

A catalyst of the empirical composition 80% $VSb_{1.2}Fe_{0.2}Ti_{0.5}$-20% $SiO_2$ was made as follows: 11.42 g $V_2O_5$ was added to a mixture consisting of 450 cc $H_2O$ and 50 g of 30% $H_2O_2$ in a 2-liter beaker, and stirred at RT about 15 minutes, until a dark red peroxy complex had formed. 21.85 $Sb_2O_3$ powder was then added, the hot plate temperature control was set to "high", and the beaker was covered with a watchglass. As it heated, the color of the slurry changed from yellow to green to black. The mixture was digested for approximately 3 hours; water was added occasionally to keep the volume constant. Thereafter, 4.35 g ferrous acetate, 4.99 g of fumed $TiO_2$ (Degussa, P-25) and 33.33 g of a 30% $SiO_2$ sol (Nissan) were added. The catalyst slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20–35 mesh size. The ground catalyst was given a final calcination at 810° C. for 3 hours. Before being evaluated in the microreactor, 8.0 g of the calcined catalyst was washed with 100 cc of isobutanol and then dried at 120° C.

EXAMPLE 38

A catalyst of the empirical formula 80% $VSb_{1.2}Cr_{0.2}Ti_{0.5}O_x$ was made in the manner of the preceding example except that $CrO_3$ was substituted for the ferrous acetate in an amount to satisfy the empirical formula.

EXAMPLE 39

A catalyst having the empirical composition $VSb_{1.4}Sn_{0.2}Ti_{0.3}O_x$ was made as follows: 26.10 g $V_2O_5$ was added to a mixture consisting of 400 cc $H_2O$ and 100 g of 30% $H_2O_2$ in a 2-liter beaker, and stirred at RT about 15 minutes, until a dark red peroxy complex had formed. 58.45 g $Sb_2O_3$ powder was then added, the hot plate temperature control was set to "high", and the beaker was covered with a watchglass. A it heated, the color of the slurry changed from yellow to green to black. The mixture was digested for approximately 3 hrs; water was added occasionally to keep the volume constant. 42.12 g of a 20.58% d $SnO_2$ sol was added, followed by 6.87 g of fumed $TiO_2$ (Degussa, P-25). The catalyst slurry was evaporated on the hot plate with constant stirring until it thickened. It was then dried at 120° C. overnight and calcined at 650° C. for 8 hours. After this, the catalyst was ground and screened to a 20–35 mesh size. The ground catalyst was given a final calcination at 810° C. for 3 hours. Before being evaluated in the microreactor, 8.0 g of the calcined catalyst was washed with 100 cc of isobutanol and then dried at 120° C.

The $SnO_2$ sol used in the above preparation of this catalyst was made as follows: 1800 ml water and 900 ml concentrated nitric acid were placed in a 4 liter beaker fitted with mag stirred and thermometer. 300 g Sn metal ($-20$ mesh) were added over 2–2.5 hours maintaining the reaction temperature at 55–60 C (not to exceed 60C). The white suspensions were stirred at room temperature overnight and then centrifuged. This separated the $SnO_2$ well and allowed the supernatant liquid to be poured off without disturbing the solids. The combined solids were suspended in water ($\sim$2.5 liters total volume). Then, the suspension was brought to pH 7 by adding 380 ml concentrated $NH_4OH$. The suspension was diluted to 3500 ml and stirred overnight. The suspension was then centrifuged again and the solids were removed, combined and diluted to 3500 ml with fresh water (first water wash). This suspension was stirred overnight and then centrifuged a third time. The water was discarded and the solids washed a second time with water (second wash) by resuspension in the centrifuge bottles. After shaking to disperse the solid, the bottles were matched in weight and centriguted a fourth time. The clear water wash was discarded. The wash water still indicated >0.5 g/liter nitrate ion using JPB's test paper from Aldrich. Consequently, a third wash was done by resuspending the solid in water in the centrifuge bottles. This wash water was a dilute milky sol after centrifuging. Solids were only 0.113% and the test paper indicated approximately 1 g nitrate/liter (diluted the wash 1:10 before using the paper). Further washing would peptize more $SnO_2$ so the process was stopped at this point. Recovered 1564.2 g of wet cake $SnO_2$ after the final wash. Make up a 20% sol by adding 117.8 g 40% methylamine solution to the wet solid, triturating to obtain a translucent grey paste and diluting the paste with 2122 g water. The trituration was not easy because of the formation of chunks of solid partly penetrated by the amine solution. These chunks were sticky, slippery and difficult to disperse. The more difficult chunks were removed from the beaker and macerated in a large evaporating dish using the bottom of a beaker to smash the lumps. The sol had some grey unreacted Sn metal in suspension and was given a final 30 minute centrifuging. This separated the metal, but the sol could not be decanted away cleanly. Consequently, the sol was filtered through glass microfiber filter paper on a buchner funnel to remove this suspended metal. Final sol was light grey-green with solids 20.58%.

EXAMPLE 42

A pre-catalyst slurry of the composition of Example 1 was prepared as in that example except on a large scale. Then a small portion of this catalyst slurry was evaporated on the hot plate with constant stirring until it thickened. It was then dried at 120° C. overnight and calcined at 290° C. for 3 hours, at 425° C. for 3 hours and at 650° C. for 8 hours. After this, the catalyst was ground and screened to a 20–35 mesh size. The ground catalyst was given a final calcination at 810° C. for 3 hours. Before being evaluated in the microreactor, 8.0 g of the calcined catalyst was washed with 100 cc of isobutanol.

The foregoing catalysts were tested in ammoxidation runs summarized in the following tables. In these runs the catalyst listed in the left-hand column was in a tubular ⅜ inch I.D. stainless steel fixed bed reactor. Pressure was slightly above atmospheric. The reactor is equipped with a preheat leg and is immersed in a temperature controlled molten salt bath. The feed was fed over the catalyst for at least one-half hour before collection of product; the runs of each example last 30–60 minutes during which the product is collected for analysis.

TABLE 1

| Catalyst Example No. | Feed Mole Ratios $C_2/NH_3/O_2/N_2/H_2O^{(3)}$ | Temp. °C. | CT Secs$^{(4)}$ | Percent Propene Conversion | Mol % Yields AN$^{(2)}$ | Selectivity %$^{(1)}$ HCN | Selectivity %$^{(1)}$ AN | Productivity$^{(6)}$ AN | By-Product Yields Mol % AA$^{(7)}$ | By-Product Yields Mol % ACR$^{(8)}$ |
|---|---|---|---|---|---|---|---|---|---|---|
| 2$^{(5)}$ | 1.8/2.2/3.6/2.4/6 | 460 | 0.27 | 74.0 | 24.2 | 21.6 | 32.6 | — | 0.39 | 0.00 |
| 40 | " | 460 | 0.40 | 98.3 | 77.5 | 6.6 | 78.8 | 0.71 | 0.53 | 0.31 |
| 13 | " | " | 0.32 | 97.7 | 76.4 | 6.7 | 78.1 | 0.59 | 0.17 | 0.04 |
| 11 | " | " | 0.57 | 98.4 | 80.7 | 6.4 | 82.0 | 0.30 | 0.42 | 0.29 |
| 3 | " | " | 0.24 | 97.4 | 76.0 | 6.7 | 78.1 | 0.58 | 0.44 | 0.54 |
| 4 | " | 445 | 0.68 | 94.9 | 72.7 | 7.2 | 76.6 | 0.21 | 0.69 | 0.19 |
| 5 | " | " | 0.59 | 94.1 | 71.7 | 8.4 | 76.2 | 0.22 | 0.61 | 0.10 |
| 7$^{(5)}$ | " | " | 1.10 | 81.7 | 48.3 | 11.4 | 59.1 | — | 0.50 | 0.20 |
| 8$^{(5)}$ | " | " | 10.8 | 92.0 | 61.1 | 10.2 | 66.4 | 0.017 | 0.37 | 0.02 |
| 9 | " | " | 0.44 | 99.5 | 71.6 | 7.6 | 72.0 | 0.34 | 0.44 | 0.02 |
| 10 | " | " | 0.44 | 97.7 | 66.6 | 8.9 | 68.2 | 0.30 | 0.43 | 0.04 |
| 4 | " | " | 0.66 | 97.8 | 71.1 | 7.6 | 72.7 | 0.22 | 0.60 | 0.15 |
| 39 | " | " | 0.56 | 94.5 | 76.5 | 6.2 | 80.9 | 0.27 | 0.57 | 0.97 |
| 6 | " | " | 0.34 | 99.3 | 74.2 | 7.7 | 74.8 | 0.53 | 0.36 | 0.14 |
| 12 | " | " | 0.33 | 98.2 | 67.3 | 10.2 | 68.5 | 0.46 | 0.65 | 0.02 |
| 14 | " | 460 | 0.44 | 99.5 | 79.1 | 6.2 | 79.4 | 0.53 | 1.04 | 0.06 |
| 14 | " | " | 0.31 | 99.1 | 78.5 | 6.4 | 79.3 | 0.58 | 0.92 | 0.21 |
| 15 | " | " | 0.51 | 98.7 | 77.3 | 7.5 | 78.3 | 0.50 | 0.62 | 0.06 |

$^{(1)}$Selectivity based on propylene
$^{(2)}$AN is Acrylonitrile
$^{(3)}$C$_3$ is Propylene
$^{(4)}$Contact Time, Seconds
$^{(5)}$Comparative Example
$^{(6)}$Pounds of AN/pound of catalyst/Hour
$^{(7)}$AA is acrylic acid
$^{(8)}$ACR is acrolein

TABLE 2*

| Catalyst Example No. | Feed Mole Ratios $C_2/NH_3/O_2/N_2/H_2O^{(3)}$ | Temp. °C. | CT Secs$^{(4)}$ | Percent Propene Conversion | Mol % Yields AN$^{(2)}$ | Selectivity % HCN | Selectivity % AN | Productivity$^{(6)}$ AN | By-Product Yields Mol % AA$^{(7)}$ | By-Product Yields Mol % ACR$^{(8)}$ |
|---|---|---|---|---|---|---|---|---|---|---|
| 16 | 1.8/2.2/3.6/2.4/6 | 460 | 0.49 | 99.1 | 70.7 | 8.6 | 71.4 | 0.32 | 0.41 | 0.08 |
| 17 | " | " | 0.54 | 97.6 | 75.8 | 7.0 | 77.7 | 0.31 | 1.03 | 0.35 |
| 1 | " | " | 0.51 | 97.7 | 74.8 | 6.8 | 76.6 | 0.51 | 1.11 | 0.27 |
| 19 | " | " | 0.35 | 98.2 | 75.9 | 7.0 | 77.3 | 0.42 | 0.68 | 0.01 |
| 20 | " | " | 0.66 | 98.4 | 75.2 | 7.3 | 76.4 | 0.40 | 0.81 | 0.16 |
| 18 | " | " | 0.54 | 98.4 | 76.5 | 7.2 | 77.7 | 0.52 | 0.47 | 0.12 |
| 21 | " | " | 0.51 | 97.3 | 75.0 | 7.3 | 77.1 | 0.52 | 0.80 | 0.28 |
| 22 | " | " | 0.51 | 99.0 | 75.8 | 7.1 | 76.6 | 0.53 | 0.60 | 0.08 |
| 23 | " | " | 0.49 | 99.3 | 75.7 | 7.0 | 76.3 | 0.53 | 0.76 | 0.11 |
| 25 | " | " | 0.22 | 95.3 | 70.4 | 7.6 | 73.8 | 0.94 | 0.60 | 0.32 |
| 35 | " | " | 0.51 | 98.7 | 75.0 | 7.2 | 76.0 | 0.52 | 0.76 | 0.14 |
| 24 | " | " | 0.34 | 97.7 | 73.6 | 7.6 | 75.4 | 0.82 | 0.71 | 0.29 |
| 26 | " | " | 0.51 | 98.4 | 76.3 | 6.9 | 77.6 | 0.53 | 0.56 | 0.16 |
| 30 | " | " | 0.63 | 98.5 | 75.1 | 7.2 | 76.2 | 0.53 | 0.62 | 0.16 |
| 28$^{(5)}$ | " | " | 2.60 | 93.3 | 62.2 | 11.4 | 66.7 | 0.09 | 0.53 | 0.07 |
| 32 | " | " | 0.47 | 98.4 | 79.8 | 5.8 | 81.1 | 0.36 | 0.73 | 0.12 |
| 31 | — | " | 0.12 | 95.2 | 65.4 | 7.4 | 68.8 | 0.87 | 0.28 | 0.22 |
| 33 | " | " | 0.24 | 98.9 | 77.7 | 6.1 | 78.6 | 0.53 | 0.60 | 0.14 |
| 29 | " | " | 3.85 | 93.2 | 65.2 | 9.8 | 70.0 | 0.06 | 0.30 | 0.03 |
| 34 | " | " | 0.22 | 98.6 | 69.6 | 9.6 | 70.6 | 0.66 | 0.28 | 0.00 |
| 36 | " | " | 0.17 | 96.6 | 71.7 | 6.5 | 74.2 | 0.95 | 0.28 | 0.26 |
| 37 | " | " | 0.36 | 94.9 | 70.2 | 8.7 | 74.0 | 0.65 | 0.29 | 0.16 |
| 38 | " | " | 0.17 | 96.8 | 67.8 | 9.1 | 70.1 | 1.36 | 0.45 | 0.15 |

*See Table 1 for Footnotes

As will be evident to those skilled in the art, various modifications of this invention can be made or followed in the light of the foregoing disclosure and discussion without departing from the spirit and scope of the disclosure or from the scope of the claims.

We claim:

1. Method for the ammoxidation of $C_3$ to $C_5$ mono-olefins to make $\alpha,\beta$-mono-unsaturated acyclic nitriles containing no acetylenic unsaturated having 3 to 5 carbon atoms and HCN by introducing such mono-olefins molecular oxygen and ammonia into a reaction zone into vapor phase contact with a solid ammoxidation catalyst, wherein the mol ratio of introduced molecular oxygen and ammonia to said introduced mono-olefin is at least 1.5 and 1.0, respectively, wherein said catalyst contains the elements and proportions indicated by the empirical formula:

$$V_1Sb_aM_mN_nO_x$$

where
- a = 0.5 to 2
- M = one or more of: Sn, Ti, Fe, and Ga
- m = 0.05 to 3
- N = one or more of: W, Bi, Mo, Li, Mg, P, Zn, Mn, Te, Ge, Nb, Zr, Cr, Al, Cu, Ce, B
- n = zero to 0.5, and wherein the preparation of the catalyst includes contacting in an aqueous dispersion a vanadium compound and an antimony compound while said vanadium is in solution.

2. A method of claim 1 wherein an $\alpha$, $\beta$-mono-unsaturated nitrile selected from propylene and isobutylene is ammoxidized to acrylonitrile and methacrylonitrile, respectively.

3. A method of claim 1 wherein m is at least 0.1.

4. A method of claim 2 wherein m is at least 0.1.

5. A method of claim 1 wherein m is at most 1.

6. A method of claim 2 wherein m is at most 1.

7. A method of claim 1 wherein m is in the range from 0.1 to 1.

8. A method of claim 2 wherein m is in the range from 0.1 to 1.

9. A method of claim 2 wherein propylene is selected.

10. A method of claim 9 wherein m is in the range from 0.05 to 1.

11. A method of claim 9 wherein m is in the range from 0.1 to 1.

* * * * *

UNITED STATES PATENT AND TRADEMARK OFFICE
CERTIFICATE OF CORRECTION

PATENT NO. : 5,258,543
DATED : November 2, 1993
INVENTOR(S) : Dev D. Suresh, et. al.

It is certified that error appears in the above-indentified patent and that said Letters Patent is hereby corrected as shown below:

Column 18, claim 1, line 3, "unsaturated" should read --unsaturation and--.
Column 20, claim 2, lines 1-2, "an $\alpha,\beta$-mono-unsaturated nitrile" should read -- " a mono-olefin"--.

Signed and Sealed this

Ninth Day of August, 1994

Attest:

BRUCE LEHMAN

*Attesting Officer*   *Commissioner of Patents and Trademarks*